US00PP35131P2

(12) United States Plant Patent
Gitzels et al.

(10) Patent No.: US PP35,131 P2
(45) Date of Patent: Apr. 25, 2023

(54) ***DAHLIA* PLANT NAMED 'BALDATEQIM'**

(50) Latin Name: *Dahlia variabilis*
Varietal Denomination: Baldateqim

(71) Applicant: Ball Horticultural Company, West Chicago, IL (US)

(72) Inventors: Jeroen Gitzels, Zwaag (NL); Hans Henrik Kampmann, Ullerslev (DK)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/989,236

(22) Filed: Nov. 17, 2022

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
CPC ... A01H 5/02; A01H 5/00; A01H 6/14; A01H 6/144
See application file for complete search history.

(56) References Cited

U.S. PATENT DOCUMENTS

PP22,907 P2 * 7/2012 Nielsen ..... A01H 6/14 Plt./321

* cited by examiner

*Primary Examiner* — June Hwu
(74) *Attorney, Agent, or Firm* — Audrey Charles

(57) ABSTRACT

A new and distinct cultivar of *Dahlia* plant named 'Baldateqim', characterized by its double-type, medium red-orange, yellow-orange, and yellow-green multi-colored inflorescences, dark green-colored foliage, and vigorous, upright-mounded growth habit, is disclosed.

1 Drawing Sheet

Latin name of genus and species of plant claimed: *Dahlia variabilis*.

Variety denomination: 'Baldateqim'.

BACKGROUND OF THE INVENTION

The present invention relates to a new and distinct cultivar of *Dahlia* plant botanically known as *Dahlia variabilis* and hereinafter referred to by the cultivar name 'Baldateqim'.

The new cultivar originated in a controlled breeding program in in Odense, Denmark during July 2015. The objective of the breeding program was the development of *Dahlia* cultivars that are freely flowering with double-type, large inflorescences and a vigorous, upright-mounded growth habit.

The new *Dahlia* cultivar is an irradiation-induced sport of DALINA Venti Tequilla Sunrise 'DAFYRRE', not patented, characterized by its double-type, light red and yellow-green colored inflorescences, medium green-colored foliage, and vigorous, upright-mounded growth habit. The new cultivar was discovered as a side shoot and selected during July 2016 in a controlled environment in in Odense, Denmark.

Asexual reproduction of the new cultivar by terminal stem cuttings since July 2016 in in Odense, Denmark, Hem, The Netherlands and Andijk, The Netherlands has demonstrated that the new cultivar reproduces true-to-type with all the characteristics, as herein described, firmly fixed and retained through successive generations of such asexual propagation.

SUMMARY OF THE INVENTION

The following characteristics of the new cultivar have been repeatedly observed and can be used to distinguish 'Baldateqim' as a new and distinct cultivar of *Dahlia* plant:

1. Double-type, medium red-orange, yellow-orange, and yellow-green multi-colored inflorescences;
2. Dark green-colored foliage; and
3. Vigorous, upright-mounded growth habit.

Plants of the new cultivar differ from plants of the parent primarily in having multi-colored inflorescences that include yellow-orange coloration unlike the parent.

Of the many commercially available *Dahlia* cultivars, the most similar in comparison to the new cultivar is Venti Golden Yellow 'DANITTEN', U.S. Plant Pat. No. 22,907. However, in side-by-side comparison, plants of the new cultivar differ from plants of 'DANITTEN' in at least the following characteristics:

1. Plants of the new cultivar have more branches per plant than plants of 'DANITTEN';
2. Plants of the new cultivar lack simple leaves unlike plants of 'DANITTEN'; and
3. Plants of the new cultivar have a ray floret color that is more red-orange colored than of plants of 'DANITTEN'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baldateqim'. The 4-month-old plants were grown in 6.5-inch pots for 10 weeks in a glass-covered greenhouse in Hem, The Netherlands. Plants were given one pinch before transplant.

DETAILED BOTANICAL DESCRIPTION

Figure 1:
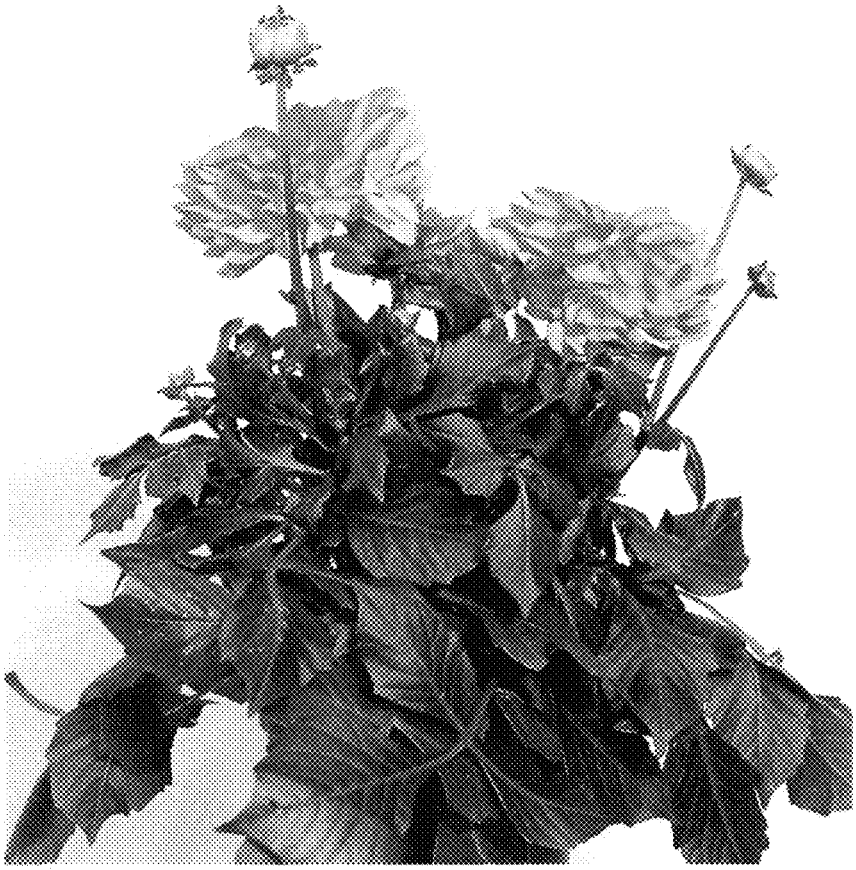
FIG. 1 illustrates a side view of the overall growth and flowering habit of 'Baldateqim'.
Figure 2:
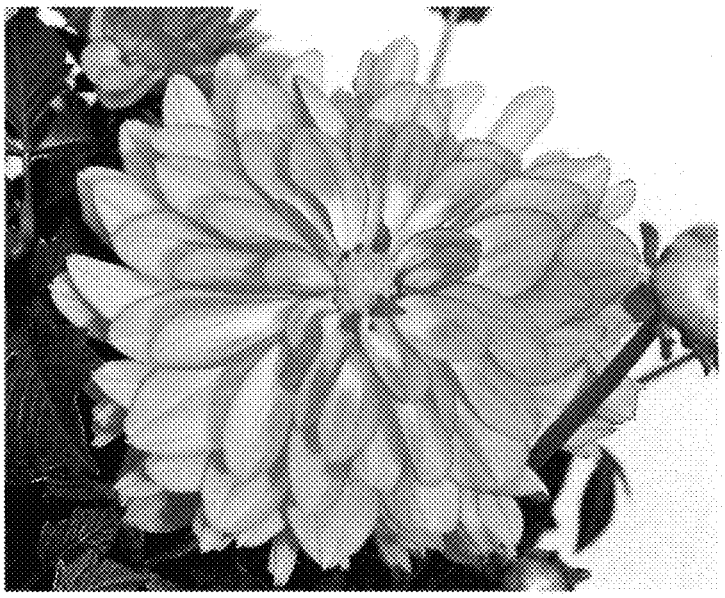
FIG. 2 illustrates a close-up view of an individual inflorescence of 'Baldateqim'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in February 2022 under natural light conditions in Boskoop, The Netherlands.

The following descriptions and measurements describe 4-month-old plants produced from cuttings from stock plants and grown in a glass-covered greenhouse under conditions comparable to those used in commercial practice. The plants were grown in Hem, The Netherlands in 6.5-inch pots for 10 weeks utilizing a soilless growth medium. Plants were given one pinch before transplant. Greenhouse temperatures were maintained at approximately 61° F. to 72° F. (16° C. to 22° C.) during the day and approximately 57° F. to 61° F. (14° C. to 16° C.) during the night. Supplemental lighting was used. Measurements and numerical values represent averages of typical plants.

Botanical classification: *Dahlia variabilis* 'Baldateqim'.

Parentage:

*Parent.*—DALINA Venti Tequilla Sunrise 'DAFYRRE', not patented.

Propagation:

*Type cutting.*—Terminal stem.

*Time to initiate roots.*—Approximately 9 to 12 days.

*Time to produce a rooted cutting.*—Approximately 25 to 32 days.

*Root description.*—Fine, fibrous.

*Rooting habit.*—Freely branching.

Plant description:

*Commercial crop time.*—Approximately 7 to 9 weeks from a rooted cutting to finish in a 15 cm pot.

*Growth habit and general appearance.*—Moderately vigorous, upright-mounded.

*Size.*—Height from soil level to top of plant plane: Approximately 32.5 cm. Height from soil level to top of foliage: Approximately 24.1 cm. Width: Approximately 36.8 cm.

*Branch.*—Quantity of lateral branches per plant: Approximately 12. Strength: Moderately strong. Length of lateral branch: Approximately 10.5 cm. Diameter of lateral branch at central internode: Approximately 6.0 mm. Length of central internode of lateral branch: Approximately 3.2 cm. Texture: Glabrous. Color: 146B slightly to moderately tinted with 183A.

Foliage description:

*General description.*—Quantity of leaves per lateral branch: Approximately 8. Type: Compound. Quantity of leaflets per compound leaf: Approximately 3, trifoliate and 5. Fragrance: Strongly spicy. Arrangement: Opposite. Aspect: Petiole mostly perpendicular angle to stem with blade slightly extending downward.

*Mature compound leaf.*—Shape: Broadly elliptic to broadly ovate in outline. Shape of terminal leaflet: Broadly elliptic to broadly ovate. Shape of lateral leaflets: Ovate to broadly ovate. Margin: Widely serrate. Apex: Acute. Base: Attenuate. Venation pattern: Pinnate. Length of mature compound leaf: Approximately 20.7 cm. Width of mature compound leaf: Approximately 19.6 cm. Length of terminal leaflet: Approximately 12.2 cm. Width of terminal leaflet: Approximately 6.7 cm. Length of lateral leaflets: Approximately 10.9 cm. Width of lateral leaflets: Approximately 5.2 cm. Texture of upper and lower surfaces: Sparsely pubescent. Color of upper surface: NN137A. Color of lower surface: N148C. Length of petiole of mature compound leaf: Approximately 5.6 cm. Diameter of petiole of mature compound leaf: Approximately 5.5 mm. Length of rachis: Approximately 11.0 cm. Texture of upper and lower surfaces of petiole and rachis: Glabrous. Color of upper surface of petiole and rachis: N148A with 147B, slightly to heavily tinted with 187A. Color of lower surface of petiole and rachis: 146A to 146B.

Flowering description:

*Flowering habit.*—'Baldateqim' is freely flowering under outdoor growing conditions with substantially continuous blooming from spring through autumn.

*Lastingness of individual inflorescence on the plant.*—Approximately 2 weeks.

Inflorescence description:

*General description.*—Type: Double, composite, consisting of multiple rows or ray florets, and disc florets, persistent. Aspect: Facing upward and outward. Arrangement: Terminal, arising from leaf axils on strong peduncles positioned over the foliage. Disc and ray florets arranged acropetally on a capitulum. Quantity per plant: Approximately 4. Fragrance: None detected. Shape: Hemispherical when ray florets are fully open. Inflorescence diameter: Approximately 11.4 cm. Inflorescence depth: Approximately 7.1 cm. Disc diameter: Approximately 2.0 cm. Receptacle diameter at base: Approximately 9.0 mm. Receptacle depth: Approximately 5.0 mm. Receptacle color: 145B and 146C.

*Peduncle.*—Strength: Strong. Aspect: Erect. Length: Approximately 19.0 cm. Diameter: Approximately 5.0 mm. Texture: Glabrous. Color: N199B, lightly striped and tinted with 146A.

*Bud.*—Rate of bud opening: Generally takes 2 weeks for bud to progress from first color to fully open flower. Quantity per plant: Approximately 11.

*Bud just before opening.*—Shape: Oblate. Depth at first color: Approximately 1.2 cm. Diameter at first color: Approximately 1.9 cm. Texture: Glabrous. Color: Outer surface of the phyllaries N144B with base of 143B and apex tinted with 174D.

*Ray florets.*—Quantity per inflorescence: Approximately 120. Arrangement: Imbricate, in multiple whorls. Aspect: Slightly concave and twisted. Shape: Obovate. Margin: Entire. Apex: Acute. Base: Attenuate. Appearance: Matte, moderately velvety. Length: Approximately 5.2 cm. Width: Approximately 2.3 cm. Texture of upper and lower surfaces: Glabrous.

Color of upper surface when first and fully open: 24B with edges and venation of 34A, base of 1B. Color of lower surface when first and fully open: 33B with centers of 33C, base of 2B. Color of upper surface before senescence: 24A to 24B with edges and venation of 34A, base of 1B. Color of lower surface before senescence: 34B with N34B base of 1C.

*Disc florets.*—Quantity per inflorescence: Approximately 50. Arrangement: Massed in center of inflorescence. Aspect: Erect. Shape: Tubular. Margin: Entire. Apex: 5 acute tips. Base: Fused. Length: Approximately 1.7 cm. Diameter at apex: Approximately 6.0 mm. Diameter at base: Approximately 1.0 mm. Texture: Glabrous. Color when fully open: 13A with midsection of 151C and 154D at base, translucent.

*Outer phyllaries.*—Quantity: Approximately 7. Aspect: Slightly twisted, nearly perpendicular to peduncle to slightly reflexed. Shape: Ovate. Margin: Entire. Apex: Acute. Base: Truncate. Length: Approximately 1.7 cm. Width: Approximately 7.0 mm. Texture of upper and lower surfaces: Glabrous. Color of upper surface: 137B. Color of lower surface: 138B with venation of 137A.

*Inner phyllaries.*—Quantity: Approximately 1 per floret. Shape: Linear, imbricate. Margin: Entire. Apex: Broadly acute to obtuse. Base: Truncate. Length of outermost: Approximately 1.8 cm. Width of outermost: Approximately 7.0 mm. Length of innermost: Approximately 1.2 cm. Width of innermost: Approximately 5.5 mm. Texture of upper and lower surfaces: Glabrous. Color of upper and lower surfaces: 150A, translucent with 143A at base of outermost.

*Reproductive organs.*—Androecium: On disc florets. Stamen quantity: 5 per floret. Stamen length: Approximately 8.0 mm. Anther shape: Linear. Anther length: Approximately 4.0 mm. Anther color: 13A. Pollen amount: Abundant. Pollen color: 23A. Gynoecium: On disc and ray florets. Pistil length: Approximately 1.4 cm. Stigma shape: 2 branched. Stigma length: Approximately 3.0 mm. Stigma width: Approximately 4.0 mm. Stigma color: 23A. Style length: Approximately 1.1 cm. Style color: 150C. Ovary length: Approximately 1.0 mm. Ovary color: 154D.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldateqim', substantially as herein illustrated and described.

* * * * *